United States Patent
Herman

Patent Number: 6,141,097
Date of Patent: Oct. 31, 2000

[54] OPTICAL MEASUREMENT OF MARINE CONDITIONS

[75] Inventor: Alex W. Herman, Lr. Sackville, Canada

[73] Assignee: Her Majesty the Queen in right of Canada, as represented by the Department of Fisheries and Oceans, Ottawa, Canada

[21] Appl. No.: 09/236,354

[22] Filed: Jan. 25, 1999

[30] Foreign Application Priority Data

Feb. 2, 1998 [CA] Canada ................................. 2228499

[51] Int. Cl.[7] .................................................. G01N 15/02
[52] U.S. Cl. ........................................ 356/335; 356/385
[58] Field of Search ................................. 356/335–343, 356/385, 379, 384; 250/559.21, 559.19, 559.32, 559.4, 577, 221

[56] References Cited

U.S. PATENT DOCUMENTS

4,637,719  1/1987  Herman .
5,818,583  10/1998  Sevick-Muraca et al. ............... 356/356

*Primary Examiner*—Robert H. Kim
*Assistant Examiner*—Tu T. Nguyen
*Attorney, Agent, or Firm*—Ronald G. Bitner

[57] ABSTRACT

An apparatus for optically measuring marine conditions comprising a tunnel defining a sampling volume for water, a laser diode line generator for generating a beam of light and reflector means for directing the beam of light across the sampling volume through the water in a direction substantially perpendicular to the direction of flow of the water, and a plurality, of photo-sensor elements of similar size disposed for receiving and measuring the intensity of the light beam after passage through the water. The effective size of each photo-sensor element (about 1 $mm^2$)is greater than the smallest particle to be detected and smaller than the largest organism to be measure. The photo-sensor elements generate an output signal providing an average level representative of turbidity of the water sample, and an rapidly changing attenuated level caused by passage of an organism or particle. Measuring the attenuation of the output signal caused by passage of a particle or organism provides a measure of the size of the particle or organism. By measuring the number of adjacent photo-sensor elements having an attenuated level caused by occlusion by an organism larger than a single photo-sensor element, the transverse size of an organism can be determined. Measurement of the transit time of an attenuated level, indicates the longitudinal size of an organism, or the rate of passage of a particle for providing a measure of the flow rate through the tunnel. Combining transverse and longitudinal size data provides a shape outline of the organism.

9 Claims, 6 Drawing Sheets

OPTICAL MEASUREMENT OF MARINE CONDITIONS

BACKGROUND OF THE INVENTION

1. Field of the Invention

This invention relates to a method and apparatus for optically measuring marine conditions, and particularly for providing a measure of the number and size of marine organisms or particles.

2. Description of the Prior Art

Fisheries and research scientists worldwide require continuous information/data on the marine food chain which dominantly consists of: phytoplankton (typically 1 to 10 $\mu$m in diameter, esd (equivalent spherical diameter)); zooplankton (typically 100$\mu$m to 20 mm, esd); and fish, where each becomes a food source for the next in ascending order. Zooplankton can be classified in two sub-categories of size: microzooplankton (typically 50 to 250 $\mu$m, esd); and macrozooplankton (typically 250 $\mu$m to 20 mm, esd). Fish can also be sub-categorized in size: fish eggs (typically 1 mm in diameter); fish larvae (typically 1 to 3 cm in length); and juvenile and adult fish of sizes larger than their larval stage. Phytoplankton and zooplankton are measured in the oceans and studied for their interrelationships and for their profound effect on fisheries. Information is required on their abundance and vertical distributions in continental shelf waters, deep oceans and inland waters. Acquiring this data accurately, continuously and with wide spatial coverage with limited ship-time is a major sampling problem.

In the past the sampling of zooplanklton has generally been accomplished by towing large plankton nets with mouth openings of approximately 0.5 to 2.0 meters and lengths of approx. 3–6 meters. Some remote sensors towed behind a ship such as conductivity cells and video cameras have also been used. Sampling phytoplankton has generally been accomplished by two methods: by taking water bottle samples and processing the water samples by fluorometric methods, and by lowering or towing electronic instruments such as a fluorometer or a light attenuance meter. The light attenuance meter is less accurate in measuring phytoplankton biomass than the fluorometer but does provide a reasonable profile of 'relative biomass' when calibrated against a fluorometer at several points in sea water.

Deployment of zooplankton sampler nets from ships is generally cumbersome, time consuming and provides limited spatial coverage. The nets clog with phytoplankton material and must be recovered after short tows of approximately 10 minutes. Vertical information is generally lost, since all the sample is integrated in the net. Designs using of multiple stacked nets can yield improved but still very limited vertical information. Remote sensing of zooplankton using conductivity cells has not proven successful since the cells are small (3 to 5 nm in diameter) and unable to sample sufficient water volume.

Video cameras are suitable for imaging and identifying zooplankton but have considerable difficulty in processing in real-time because of the large volume of data, and are difficult to operate since they require spatial lighting, and can only be towed at slow speeds of 1–2 knots. Obtaining simultaneous data on zooplankton and phytoplankton and smaller fish larvae is often not done since it requires the addition of other instrumentation thereby increasing complexity and cost.

A common problem encountered by devices using light beams to count particles is the presence of 2 or more particles in the light beam resulting in a single count. The 'coincidence' problem is dependent on both the size of the light beam and the density of particles in the water.

A method and apparatus for the optical measurement of marine conditions is disclosed in applicant's earlier U.S. Pat. No. 4,637,719. The prior device could not determine the shape of an organism for identification, and was capable of detecting a relatively narrow organism/particle size range, limited to organism size above 250 $\mu$m, and could not determine the water speed. Also, the prior device was subject to the 'coincidence' problem referred to above, and was sensitive to vibration at sizes less than 200 $\mu$m.

SUMMARY OF THE INVENTION

An object of the present invention is to provide a device capable of counting and sizing a broad size range of marine organisms and/or particles with a single instrument.

It has been found that a broad size range of marine organisms and/or particles can be counted and sized with a single instrument by an optical system in which the receiver comprises an array of photo-sensor elements wherein the size of individual photo-sensor elements is selected to be greater than the smallest organism and smaller than the largest organism to be measured. The attenuation of signal form a single sensor element allows determining size information of smaller organisms/particles while the attenuation of a signal of two or more adjacent sensor elements allows determining size and shape information about organisms larger than an individual sensor element. Utilizing a plurality of relatively small sensor elements., reduces the likelihood of two or more particles being- misinterpreted as a single count.

The present invention provides an apparatus for optically measuring marine conditions comprising,: means deeming a sampling volume of water, means for generating a beam of light having a generally rectangular cross-section: means for directing said beam of light across said sampling volume through the water in a direction substantially perpendicular to the direction of flow, of the water: a substantially linear array of photo-sensor elements for receiving and measuring the intensity of the light beam after passage through the water, the effective size of each photo-sensor element being treater than the smallest particle to be detected and smaller than the largest organism to be measured; said photo-sensor elements generating an output signal providing an average level representative of turbidity, of the water, and a rapidly changing attenuated level caused by passage of an organism or particle; means for measuring the attenuation of the output signal of each photo-sensor element caused by passage of a particle or organism for indicating the size of the particle or organism; means for determining if adjacent sensor elements have an attenuated level for indicating the passage of a relatively large organism extending beyond the transverse boundary of a single sensor element and for determining the transverse size of the organism; and means for measuring the transit time of an attenuated level, for indicating the longitudinal size of an organism, or the rate of passage of a particle for providing a measure of the flow rate of the sampling volume.

DESCRIPTION OF THE PREFERRED EMBODIMENT

Figure 1:
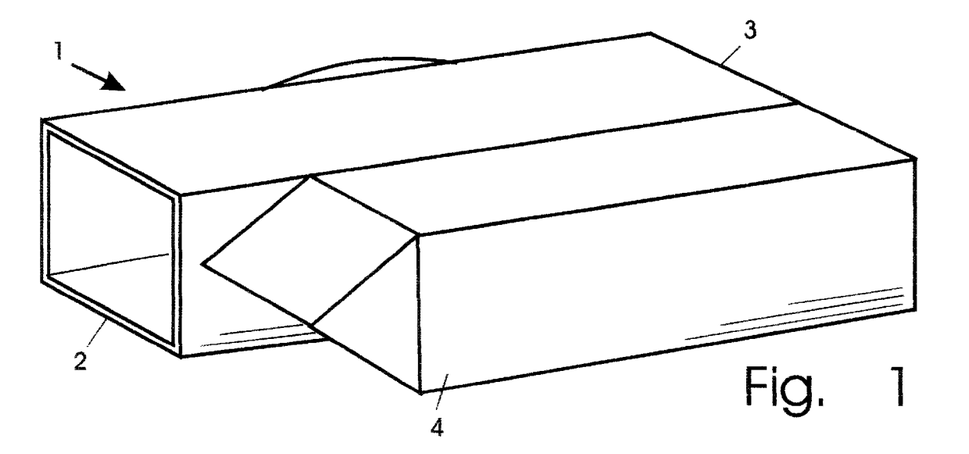
FIG. 1 is a schematic representation of one embodiment of the invention.

With reference to FIG. 1, the present invention comprises means defining a sampling volume of water in the form of a tunnel 1 having an inlet 2 and outlet 3 to allow passage of water containing organisms and particles. Associated with the tunnel 1 is a housing 4 for optic and electronic components.

Figure 2:
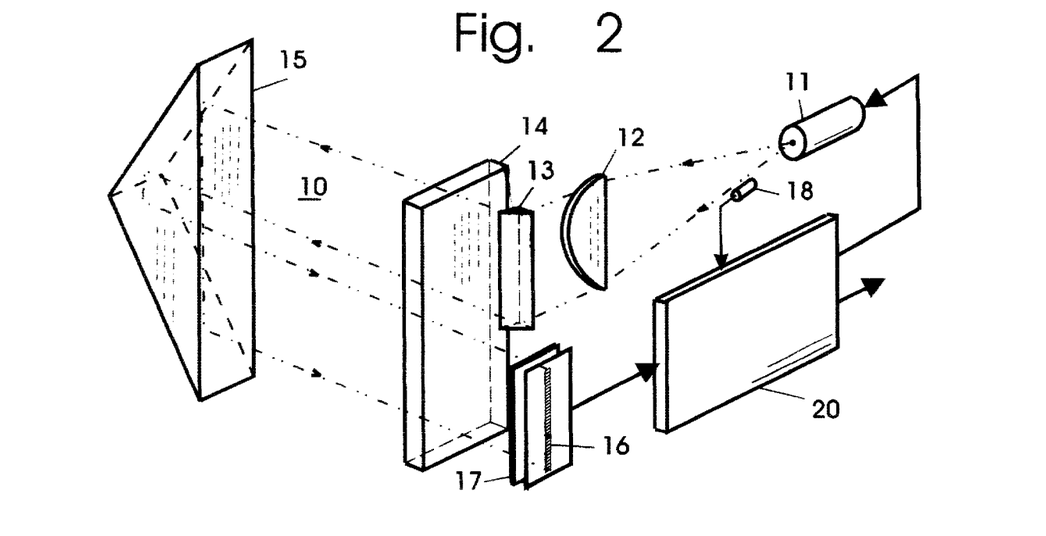
FIG. 2 is a schematic representation of one embodiment of the invention showing the optics and electronics of the apparatus.

FIG. 2 shows the optic and electronic components which includes a light source in the form of laser diode line generator 11 providing a generally rectangular beam of coherent monochromatic light, and a cylindrical lens 12 for producing a parallel beam which is directed to the water via a reflecting mirror 13 and through a transparent window 14 in the tunnel providing an air/water interface. The beam traverses the sampling volume 10 and is reflected back by a reflecting prism 15 The returning beam passes through the window 14 and is received by the photo-sensor array 16, after passing through a suitable filter 17 as will be described. A suitable microprocessor/microcontroller 20 processes the output of the photo-sensor array 16 and also controls the light source 11 in conjunction with a monitor photo-diode 18, as will be described.

The use of the mirror 13 and prism 15 allows a more compact arrangement of optical components reducing the frontal cross-sectional area of the housing 4 for reduced drag for towing. The prism 15 also eliminates the need for two housings on opposite sides of the chamber 1.

The measurement of organism size accurately requires that the light beam intensity remains constant when no particles or organisms to be measured are present. The light intensity received can vary as a result of the turbidity of the water which in the upper ocean is usually caused by microscopic phytoplankton particles. In order to compensate the average light intensity received is measured at 0.5 to 1 second intervals from the multi-element photo-sensor by the microprocessor which provides feedback control to the laser diode output, ie, if the light decreases the microprocessor increases the laser output to maintain a constant light output received at the photo-sensor. The light output from the laser therefore will vary in some proportion to the water turbidity and by monitoring the laser output, for example with the use of a monitor photodiode 18 as shown in FIG. 2., the light attenuance can be measured continuously.

The dimensions of the light beam and photo-sensor elements are selected to provide sensitivity, for the size range of organisms and particles to be measured. Suitable dimensions for the organisms particles of interest were found to be a photo-sensor array containing 35 elements of 1 mm height and 4.5 mm width. A light beam of 1 mm width provides a measuring area of 1×1 mm or 1 $mm^2$ for each element.

It should be noted that the effective area may be less than the physical area of the photo-sensor. For example, the effective width of the photo-sensor may be determined by the width of the light beam. The width of the light beam may be made less than the width of the photo-sensor to avoid spurious variations in the output signal as the result of vibrations. Specifically, spurious signals would arise if the illuminated area shifted into and out of the outer edges of the photo-sensor as the result of vibration in the various optical components. Hence, reference to the effective size of the photo-sensor herein refers to the illuminated or active area of the photo-sensor. The adverse effects of vibration could also be avoided by using a light beam sufficiently wider than the photo-sensors, provided the beam is uniform.

While the dimensions of the photo-sensor elements may vary with the type of organisms and particles to be measured, it appears that useful results can be obtained with an effective or illuminated photo-sensor element size range of from 0.5 to 2 $mm^2$.

It was found that a non-uniform, and specifically a bell shaped, distribution of light intensity across its width provides improved detection for small particles as compared with a light beam of uniform intensity and equal area and response from a photo-sensor. A small particle, for example, 100 microns in diameter, situated at the centre of the photo-sensor, will block considerably more light per unit area while in the laser beam than if it were situated in a uniform light beam. Note that for a particle of the same size as the photo-sensor element, for example, 1×1 mm, all the light is blocked in both cases, the laser and the uniform light source. Therefore for large particles the response function are similar. However for small particles, the use a of a bell shaped distribution of light can improve the area detection by almost 2 ½ times.

Figure 3A:
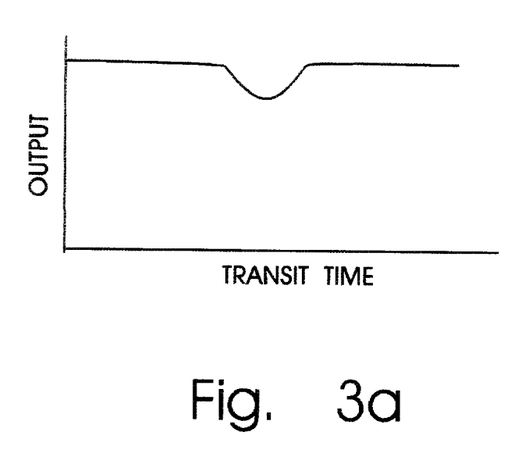
FIG. 3a and 3b are schematic representation of the output produced from organisms of different size, with FIG. 3 (a) showing the output from a smaller organism and FIG. 3 (b) showing the output from a larger organism.
Figure 3B:
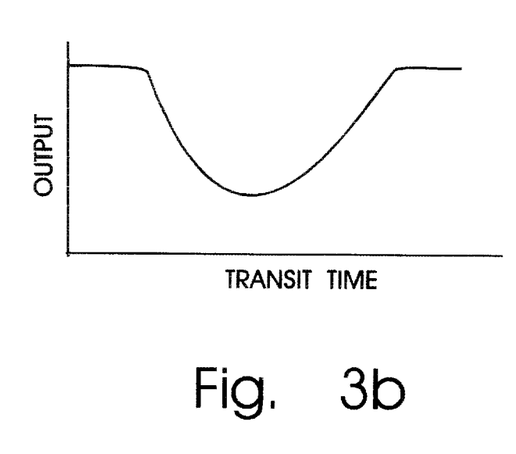

FIG. 3 shorts the basic principle of measurement of organism size. Organisms of different sizes pass through the light beam and attenuates the light to different degrees and thereby produces a signal corresponding to their size, shape and speed. FIG. 3 (a) shows the output from a smaller organism while FIG. 3 (b) shows the output from a larger organism. The change in light response on the photo-sensor will result in attenuation which is proportional to the area of the particle.

The area or size of the organism can be calculated from the following relationship:

Organism area/ Illuminated photo-sensor area = Attenuated light response/ Full light response. The individual elements of the photo-sensor array are scanned (for example at a rate of 1 MHz), and it can be seen in FIG. 3 that the transit time through the photo-sensor can be measured and logged. Since the transverse photo-sensor distance is known (ie, 1 mm), the particle speed, and hence the water flow speed, can be estimated.

Figure 4A:
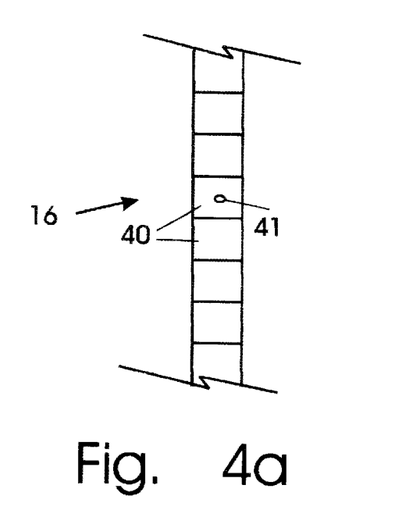
FIG. 4a and 4b are schematic representation showing a portion of the photo-sensor array and particles or organisms of different size.
Figure 4B:
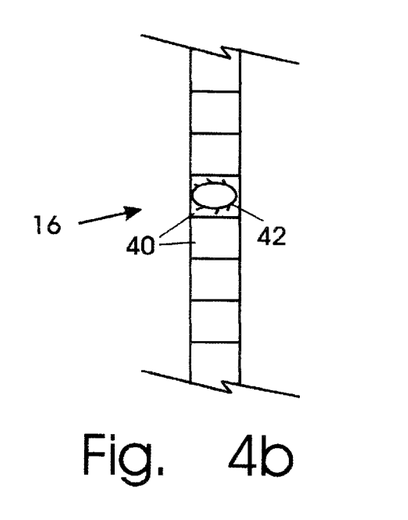

FIG. 4 shows the photo-sensor array and particles or organisms of two different sizes. FIGS. 4 (a) and 4 (b) show particles,/organisms 41 and 42 smaller than individual photo-sensor elements 40, which provide outputs such as shown in FIG. 3 (a) and 3 (b), respectively.

Figure 5:
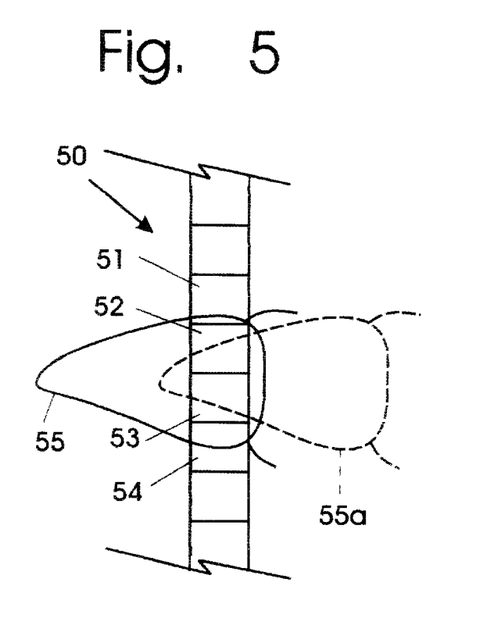
FIG. 5 is a schematic representation showing a portion of the photo-sensor array and an organism at two different times as the organism traverses the photo-sensor.
Figure 6A:
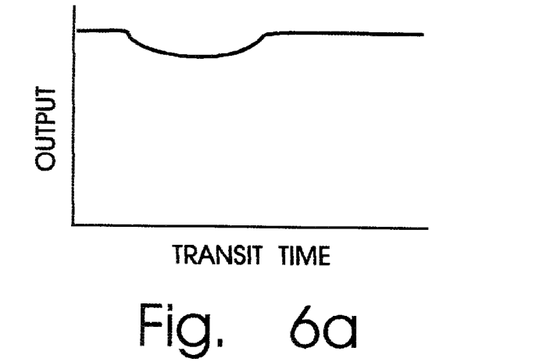
FIG. 6a, 6b, 6c, and 6d shows the output produced at four adjacent elements, designated 51, 52, 53, and 54, respectively, of the photo-sensor array shown in FIG. 5, as the organism traverses the photo-sensor array,.
Figure 6B:
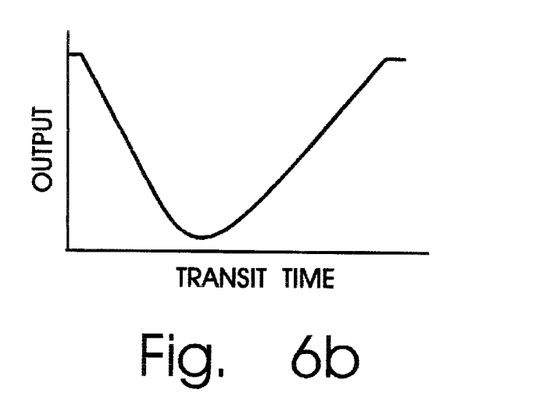
Figure 6C:
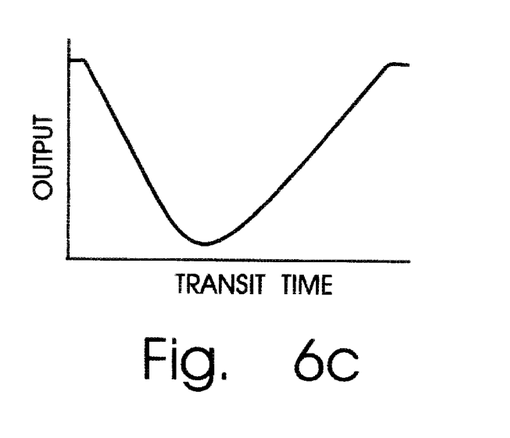
Figure 6D:
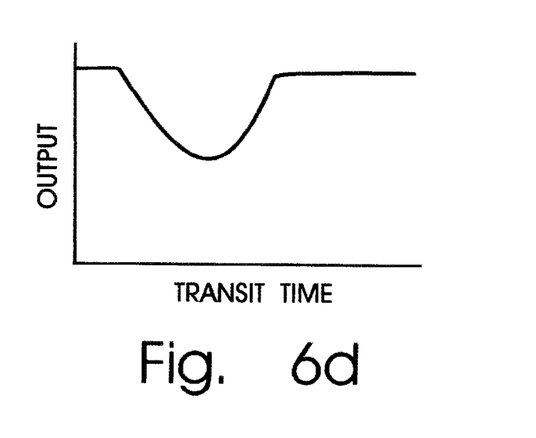

FIG. 5 shows the photo-sensor array and an organism at two different times 55 and 55a, as the organism traverses the photo-sensor 50. It can be seen that the traversing organism being wider than one element will result in the attenuation of more than one adjacent photo-sensor element, specifically elements 51 to 54. FIG. 6a, 6b, 6c, and 6d shows the output produced at four adjacent elements 51, 52, 53, and 54, respectively, of the photo-sensor array 50, shown in FIG. 5, as the organism traverses the photo-sensor array.

With reference to FIGS. 5 and 6, it can be seen that the organism 55 occludes a total of four elements simultaneously, 2 partially and 2 entirely. From the trio central elements, 52 and 53, which are entirely occluded for a period of time, it can be determined that the particle must be at least 1 mm in length and at least 2 mm in width. More precise information of the width of the organism, at any particular point along its length can be derived from the combined output (6a to 6d) of all four adjacent occluded elements 51 to 54, at the corresponding time. The length of the organism can be determined from the transit time, as discussed herein with reference to measuring water speed. Therefore, by combining the length measurement with the sectional width measurements it is possible to outline a specific shape of the organism. The resolution will be dependent on the scan rate and tow speed. At tow speeds of 10–12 knots 6–7 sections were obtained, while at 1 knot, 70–80 sections could be obtained.

Using this principle, it is also possible to measure shape of particles less than 1 mm. Particles of 0.5 mm in size (and greater) often overlap 2 elements and thus allow estimation of shape outline.

The examples shown in FIGS. 4 and 5 indicate that the present invention allows measuring the average cross-sectional area of particles and organisms from about 40 microns to about 4 cm. Furthermore the present invention also allows measuring the shape outline, and hence particle identification, for sizes greater than approximately 0.5 mm.

A common problem encountered by devices using light beams to count particles is the presence of two or more particles in the light beam resulting in a single count. The 'coincidence' problem is dependent on both the size of the light beam and the density of particles in the water. The present invention reduces the problem by partitioning the light beam at the photo-sensor into 35 elements each of 1×1 mm in effective size. By examining each element of the photo-sensor separately, it is possible to detect the presence of two or more particles in the light beam since they will be separated by the photo-sensor. In comparison to the prior generation of devices, the present arrangement improves significantly the ability to single particles in high density regions. It was found that the present invention allows operation in concentrations of about 1 million particles per cubic meter without coincidence counts or about a factor of 100 improvement over the device described in applicant's prior U.S. Pat. No. 4,637,719 referred to above.

Following is an example of one embodiment for processing data for size measurement. The processing of data obtained from 35 photo-sensor elements utilized several algorithms. One algorithm processed the cross-sectional area of each zooplankton passing across the element. The photo-sensor output voltage was digitized at a rate of 1 MHz. The data was filtered by 2 equations:

Filter No.1(present data)=0.30×Filter No.1(previous data)+0.70× raw voltage (present data).     1)

Filter No.2(present data)=0.95×Filter No.2(previous data)+0.05× raw voltage (present data).     2)

Filter No. 2 provides heavily filtered low response data which represents the average DC light levels, or average ambient light. If the turbidity of the seawater varies, then the amount of light received by the photo-sensor also varies and therefore the measurement of particle sizes would not be valid. The received light should remain constant and so the microprocessor will adjust the laser current to maintain a constant received light.

Filter No. 1 was a fast response filter and detects AC voltage changes caused by organisms or particles passing across the photo-sensor. The difference of Equation 1 and 2 (ie voltage change minus background) represents the peak voltage change representing the size (area) of the particle. A detection threshold voltage was preset within the algorithm to detect the particles. The minimum threshold was preset to 10 millivolts corresponding to about 40 microns. Once a voltage change of sufficient magnitude, signifying the presence of a particle, has been detected, filter No. 2 is held constant, that is, there is no further data input so as to allow filter No. 2 to be more representative of background levels.

A second algorithm processed the shape outline of particles greater than 0.5 mm, that is, particles which overlap several photo-sensor elements simultaneously. This algorithm also uses Filters 1 and 2, as described above, but also tracks photo-sensor elements which are active (ie. currently measuring a passing particle) and are simultaneous in time. The algorithm measures four parameters for each element: 1) the area measured, 2) the arrival time 3) the transit time of each particle. and the number of adjacent elements occluded. All of these parameters of all elements are combined to form the shape outline of the object, as described above.

Figure 7:
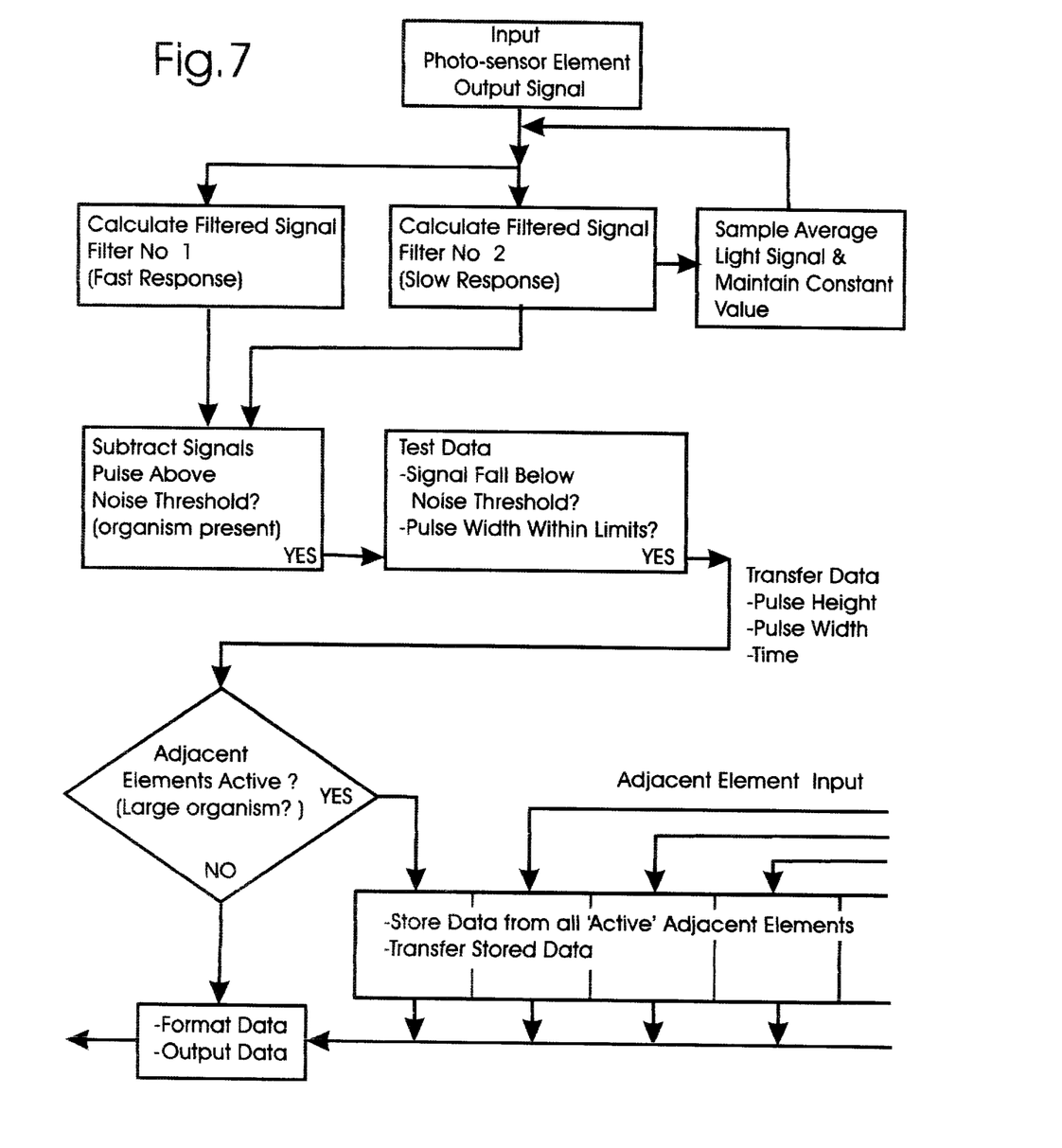
FIG. 7 is a flow chart illustrating the processing of data from a single photo-sensor element.

FIG. 7 is a flow chart illustrating the processing of data from a single photo-sensor element and the association with other elements.

Figure 8:
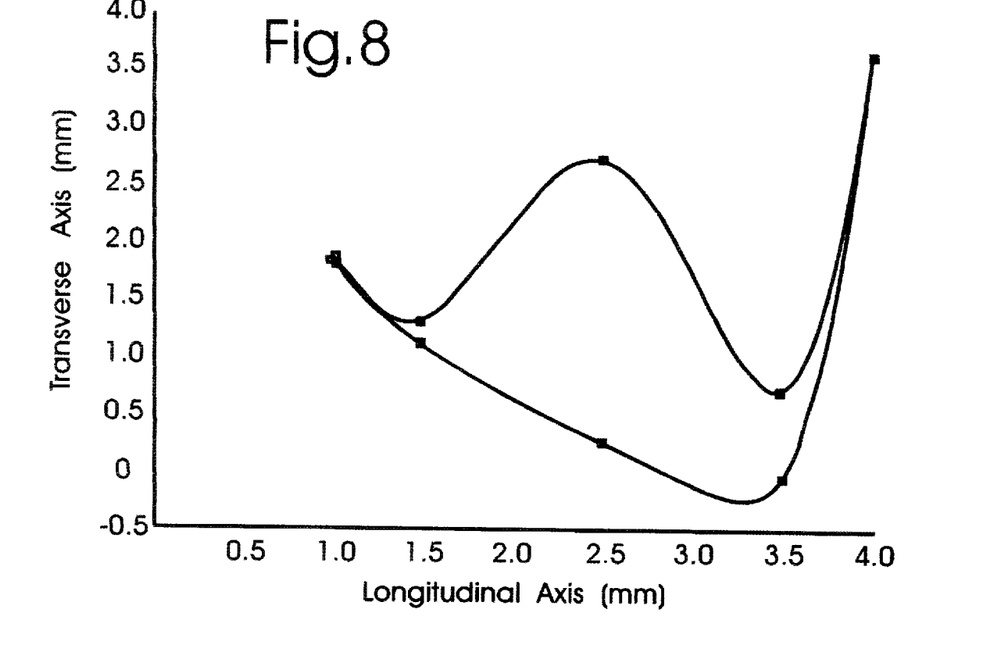
FIGS. 8 and 9 each show the shape outline of an organism obtained utilizing the present invention.
Figure 9:
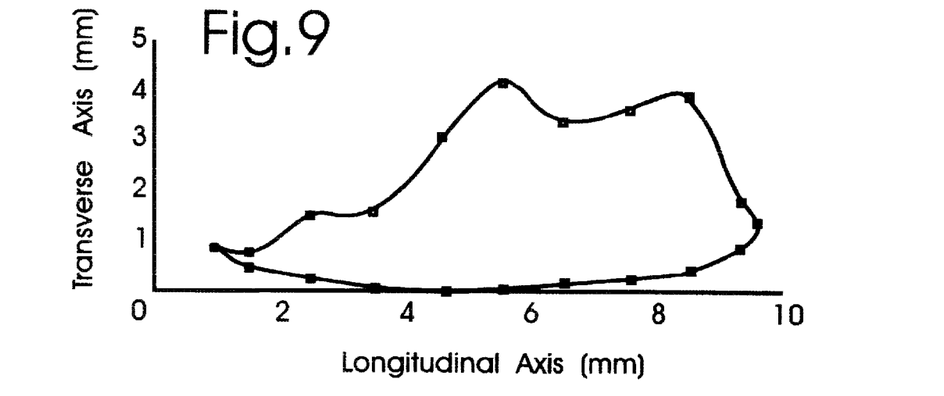

FIGS. 8 and 9 show the shape outlines of organisms obtained utilizing the above algorithms. The results indicate the ability to measure not only the shapes of these species but also their antennae and tails thereby allowing identification of the species.

The zooplankton shown in FIGS. 8 and 9 are a copepod (*Calanus finmarchicus* Stage V) and a euphausild (*Meganyctiphanes norvegica*), respectively. The square data points shown in FIGS. 8 and 9 are derived from adjacent photo-sensor elements.

Figures 10, 11A:
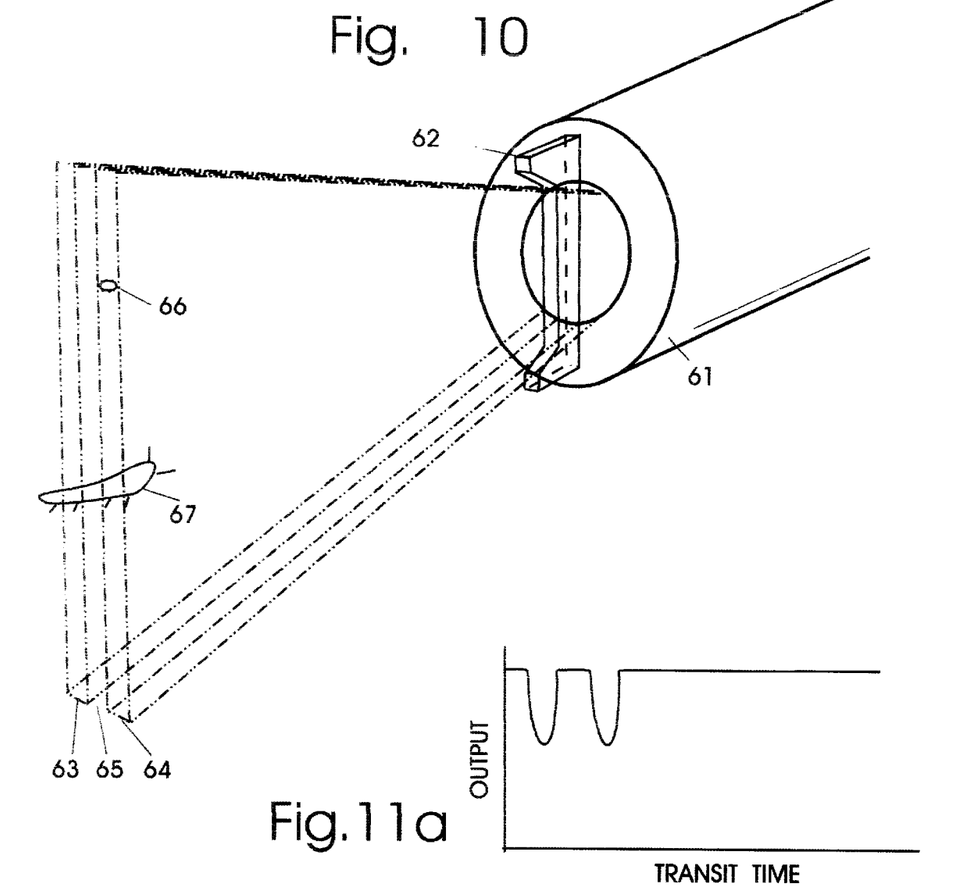
FIG. 10 is a schematic representation of a portion of another embodiment of the invention showing the light source providing a split beam.
FIGS. 11a and 11b are a schematic representation of the output produced with the embodiment shown in FIG. 10, from organisms of different size, with FIG. 11a showing the output produced from a smaller organism and FIG. 11b showing the output from a larger organism.

FIG. 10 shows schematically a portion of another embodiment of the invention in which the light source 61 provides two parallel elongated beams of light 63 and 64. In FIG. 10 a single beam from source 61 is split by suitable means shown in the form of a shim 62 near the light source 61 to produce three sections or bands 63, 64, and 64 comprising two spaced parallel elongated bands of light 63 and 64 on either side of a band 65 without light. Suitable dimensions are a shim 62 having a thickness of 0.33 mm to space the two bands 63 and 64 a distance of 0.33 apart, and with each band having a thickness of 0.33 mm.

Figure 11B:
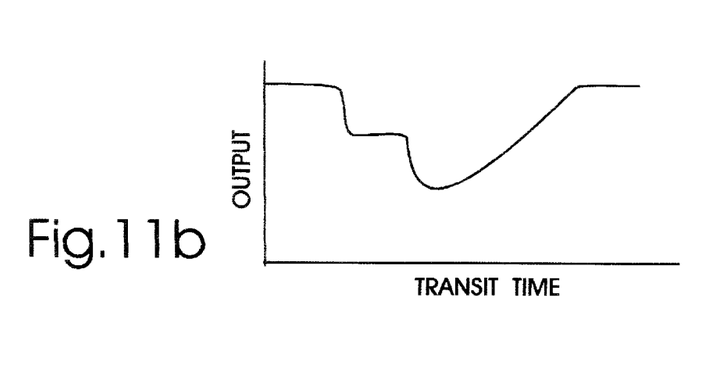

FIGS. 11a and 11b shows the output produced with the embodiment shown in FIG. 10 for organisms of different size, with FIG. 11a showing the output from a smaller organism 66 and FIG. 11b showing the output from a larger organism 67.

This arrangement provides greater sensitivity in 'shape information' of organisms passing through the beam.

Whereas in the first embodiment, the single beam configuration provides 'shape' information for organisms greater than 1 mm, the split beam configuration provides 'shape' information for organisms greater than 0.33 mm since the responses changes occur in the first 0.33 mm band of light encountered by the organism. Other advantages of the split beam design are a slight increase in size (area) sensitivity by about ⅓ and improvements in measuring transit speed. It should be noted that this embodiment with two light beams requires considerably more computing power from the onboard microprocessor. The split beam embodiment is effective for total beam lengths of about 20 cm after which fringe effects deteriorate the beam shape.

It will be understood that the invention can take different forms from that illustrated and described above, including a different physical structure that defines the sampling volume and associated housings, a different arrangement of optical components and modification of the processing of data, depending on the specific application.

What is claimed is:

1. An apparatus for optically measuring marine conditions comprising:

means defining a sampling volume of water containing particles and/or organisms;

means for generating a beam of light having a generally rectangular cross-section;

means for directing said beam of light across said sampling volume through the water in a direction perpendicular to the direction of flow of the water;

a linear array of photo-sensor elements for receiving and measuring intensity of the light beam after passage through the water, the photo-sensor elements each having an effective size greater than the smallest of the particles to be detected and smaller than the largest of the organisms to be measured;

said photo-sensor elements generating an output signal providing an average level representative of turbidity of the water, and a rapidly changing attenuated level caused by passage of an organism or particle;

means for measuring attenuation of the output signal of each photo-sensor element caused by passage of a particle or organism for indicating the size of the particle or organism;

means for determining if adjacent sensor elements have an attenuated level for indicating the passage of a relatively large organism extending beyond a transverse boundary of a single sensor element and for determining transverse size of the organism; and means for measuring transit time of an attenuated level, for indicating longitudinal size of an organism, or rate of passage of a particle for providing a measure of flow rate of the sampling volume.

2. The device of claim 1, further comprising feedback circuit means responsive to the average level of the output signal for controlling the means for generating a beam of light for providing a substantially constant light level directed to the photo-sensors.

3. The device of claim 2 wherein the feedback circuit has a time constant that is long relative to the length of a change in attenuance level produced by passage of a particle or organism.

4. The device of claim 1, wherein the effective size of each photo-sensor element is from about 0.5 to 2 $mm^2$.

5. The device of claim 1, wherein the effective size of each photo-sensor element is about 1 $mm^2$.

6. The device of claim 1, wherein the beam of light is coherent monochromatic light.

7. The device of claim 1, comprising two spaced parallel elongated beams of light.

8. The device of claim 1, wherein the means defining a sampling volume of water comprises a tunnel.

9. The device of claim 1, further comprising an enclosure for optic and electronic components attached to the tunnel.

* * * * *